United States Patent [19]

Kwiatek et al.

[11] Patent Number: 4,710,191
[45] Date of Patent: Dec. 1, 1987

[54] THERAPEUTIC DEVICE FOR THE ADMINISTRATION OF MEDICAMENTS

[75] Inventors: Alfred Kwiatek, New York, N.Y.; Jack W. Schwartz, Burlington, Vt.

[73] Assignee: Jonergin, Inc., Swanton, Vt.

[21] Appl. No.: 809,483

[22] Filed: Dec. 16, 1985

[51] Int. Cl.⁴ .............................................. A61K 9/00
[52] U.S. Cl. .................................... 604/897; 604/304
[58] Field of Search ............... 604/304, 307, 896, 891, 604/892, 897; 206/531

[56] References Cited

U.S. PATENT DOCUMENTS

| | | |
|---|---|---|
| 2,235,436 | 3/1941 | Laub . |
| 2,561,071 | 7/1951 | Prisk . |
| 3,797,494 | 3/1974 | Zaffaroni ........................ 604/897 |
| 3,814,095 | 6/1974 | Lubens . |
| 3,972,995 | 8/1976 | Tsuk et al. . |
| 4,052,505 | 10/1977 | Higuchi et al. . |
| 4,117,841 | 10/1978 | Perrotta et al. . |
| 4,176,664 | 12/1979 | Kalish . |
| 4,268,497 | 5/1981 | Griffin et al. . |
| 4,297,995 | 11/1981 | Golub . |
| 4,341,208 | 7/1982 | Gordon . |
| 4,379,454 | 4/1983 | Campbell et al. . |
| 4,402,696 | 9/1983 | Gulko . |
| 4,460,368 | 7/1984 | Allison et al. . |
| 4,460,370 | 7/1984 | Allison et al. . |
| 4,460,372 | 7/1984 | Campbell et al. . |
| 4,468,194 | 12/1984 | Ferrara . |
| 4,486,193 | 12/1984 | Shaw et al. . |

FOREIGN PATENT DOCUMENTS 0008545 3/1980 European Pat. Off. ............ 206/531

Primary Examiner—C. Fred Rosenbaum
Assistant Examiner—Jerome R. Smith, Jr.
Attorney, Agent, or Firm—Lerner, David, Littenberg, Krumholz & Mentlik

[57] ABSTRACT

A therapeutic device in the nature of a transdermal administration system is disclosed for administration of a medicament to the skin or mucosa of a host. The device is provided with a reservoir for containment of the medicament which is isolated by means of a peelable heat sealed area with respect to an adhesive layer provided for adhering the device to the host. In this manner, contamination and deterioration of the adhesive layer, contamination of the active agent, and trapping of the active agent in the adhesive layer are all avoided.

16 Claims, 3 Drawing Figures

THERAPEUTIC DEVICE FOR THE ADMINISTRATION OF MEDICAMENTS

BACKGROUND OF THE INVENTION

The present invention relates in general to a therapeutic device for the administration of a medicament or active agent to a host upon adhesion thereto by an adhesive layer. More particularly, the therapeutic device allows for topical or systemic administration to the host, or administration through the skin or mucosa of the host over a period of time, while isolating the medicament or active agent contained within a reservoir from the adhesive layer during storage and administration of the medicament or active agent to prevent the contamination of the active agent, to prevent deterioration of the adhesive and to avoid trapping of the drug within the device itself.

Transdermal administration system are known in the art. For example, Ciba-Geigy's Transderm ®-Nitro and Transderm ®-V systems have been approved for transdermal administration of nitroglycerin and scopolaimine, respectively. Similar such devices are also described, for example, in U.S. Pat. Nos. 4,460,368, 4,460,370, 4,460,372, 4,379,454, 4,486,194 and 3,972,995.

Characteristically, those controlled continuous transdermal devices known before the present invention contained a backing member which defined the outer surface of the device, a membrane sealed to the backing member to create a reservoir therebetween containingg the active agent, and an active agent permeable adhesive layer on the membrane defining the other face. Alternatively, the active agent, rather than being in one separate reservoir, is contained in a plurality of microcapsules distributed throughout the permeable adhesive layer. In either case, the active agent is delivered continuously from the reservoir or microcapsules through the membrane into the active agent permeable adhesive, which contacts the skin or mucosa of the recipient. Thus, in such devices, substantially the entire face, or surface, in contact with the skin or mucosa consists of the active agent permeable adhesive through which the active agent is administered. While such devices have a number of advantages, including full contact to the skin, certain potential disadvantages are apparent therewith.

For example, unless due care is exercised, contamination of the permeable adhesive layer can easily occur by finger contact when a user applies the device to the skin. Thus, where the fingers are sufficiently contaminated with perspiration, body oils and foreign matter, the resulting contamination of the permeable adhesive layer may adversely affect its permeable nature and cause a deterioration of its adhesive nature. This can also adversely affect the desired predetermined rate of transport of the active agent to the recipient, loss of its effecitveness, and can potentially cause infection to occur. Moreover, finger contact with the permeable adhesive layer will contaminate the finger with the active agent. This is undesirable, for example, where the active agent is an eye irritant such as scopolamine, subsequent contact of the contaminated finger to the eye may result in irritation.

In addition, contact between the adhesive layer and the active agent can also result in contamination of the active agent itself, with obvious deleterious effects, including loss of its effectiveness and the potential to cause infection or other such adverse effects upon the recipient. Furthermore, the construction of the known devices generally maintain the permeable adhesive layer in contact with the active agent contained within the reservoir during storage of the device from the time of its manufacture. Thus, there is a need for the permeable adhesive layer to be formulated specifically to match the drug or active agent, i.e., so that it will permit the drug to pass therethrough without trapping the drug, or becoming a "sink" therefor.

SUMMARY OF THE INVENTION

It is broadly an object of the present invention to provide a therapeutic device for administering medicaments or active agents to the skin or mucosa of a host which overcomes or avoids one or more of the foregoing disadvantages resulting from the use of the above-mentioned known transdermal devices. Specifically, it is within the contemplation of one aspect of the present invention to provide a therapeutic device for administering medicaments or active agents through the skin or mucosa of a host, which therapeutic device is in the nature of a transdermal administration system adapted for isolating the medicament or active agent from the adhesive layer in order to avoid the need to carefully select an adhesive which is entirely compatible with the active agent, to prevent contaminationof the active agent during either storage or administratin itself, to prevent deterioration, decomposition or contamination of the adhesive layer, including contamination by the active agents, and to prevent trapping of the active agent in the adhesive layer.

Another object of the present invention is to provide a therapeutic device for administering medicaments to the skin or mucosa of a host which, during storage, isolates the reservoir containing the medicament from the adhesive layer by a peelable, heat sealed area.

Another object of the present invention is to provide a therapeutic device for adminstering medicaments to the skin or mucosa of a host which permits the lowering of certain manufacturing costs. That is, elimination of the need for the formulation of a specific, compatible adhesive for the particular active agent in question in and of itself would reduce such costs. Moreover, the ability to utilize stronger, cheaper and more readily available impermeable adhesive in and of itself will simplify and reduce the cost of manufacturing these devices. Furthermore, this ability will also permit the use of less expensive layers or release layers, i.e., again because stronger "standard" adhesives can now be utilized therewith.

In accordance with one embodiment of the present invention there is provided a device for the administration of an active agent to the skin or mucosa of a host. The device includes a reservoir containing the active agent, a release layer formed on the inner surface of the reservoir, an active agent impermeable backing layer formed on the outer surface of the reservoir, with the backing layer overlying the release layer and sealed about a circumferential sealed area so as to endorse the reservoir, the backing layer and the release layer extending peripherally beyond the sealed area about its entire periphery so as to create an extended peripheral area, and adhesive means disposed between the backing layer and the release layer in the extended peripheral area, and thereby separated from the reservoir containing the active agent by the sealed area, the adhesive means adapted to adhere the device to the skin or mucosa of the host upon removal of the release layer, whereby the active agent is released from the reservoir to provide a dose of the active agent.

In accordance with one embodiment of the device of the present invention, the backing layer includes a heat sealable layer in contact with the release layer within the sealed area.

In accordance with another embodiment of the device of the present invention, the backing layer is a coextruded layer of a primary backing layer impermeable to the active agent and a heat sealable layer in contact with the release layer in the sealed area.

In accordance with another embodiment of the device of the present invention, the backing layer includes a primary backing layer impermeable to the active agent and extending at least to the sealed area and a secondary outer backing layer overlying the primary backing layer and the extended peripheral area. In a preferred embodiment, the adhesive means is an adhesive layer extending over the entire inner surface of the secondary outer backing layer. Preferably, the adhesive layer in this case is substantially impermeable to the active agent.

In accordance with another embodiment of the device of the present invention, the device includes an active agent permeable membrane disposed between the reservoir and the release layer, and extending at least to the sealed area so as to be sealed between the backing layer and the release layer.

In accordance with another embodiment of the device of the present invention, the sealed area comprises a peelable heat seal so that removal of the release layer is facilitated therby.

In accordance with a preferred embodiment of the device of the present invention an annular gap is provided in the extended peripheral area between the sealed area and the adhesive means in order to further separate the adhesive means from the reservoir.

BRIEF DESCRIPTION OF THE DRAWINGS

The above description, as well as other objects, features and advantages of the present invention will be more fully understood by reference to the following detailed description of the presently preferred, but nonetheless illustrative, therapeutic device for administering medicaments through the skin or mucosa of a host in accordance with the present invention, when taken in conjunction with the accompanying drawings, wherein.

DETAILED DESCRIPTION

Figure 1:
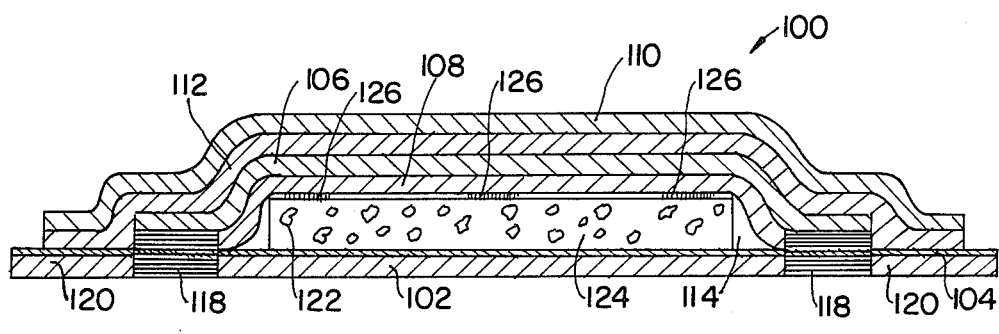
FIG. 1 is a side, elevational, cross-sectional view of one embodiment of a therapeutic device constructed in accordance with the present invention.

Referring now to the drawings, wherein like reference numeals represent like elements, there is shown in FIG. 1 one embodiment of a therapeutic device constructed in accordance with the present invention and designated generally by reference numeral 100. The device 100 is constructed of a plurality of layers including an active agent impermeable heat sealable release layer 102 which is coated with a release coating 104 on the inner surface thereof (e.g., a silicone release coated polyethylene film), an active agent impermeable backing layer 106 co-extruded with a heat sealable layer 108, and an outer backing layer 110 supporting an active agent impermeable pressure sensitive adhesive layer 112. A distinct reservoir 114 is formed by heat sealing the backing layer 106 about its entire perimeter to the underlying release layer 102 by means of the interposed heat sealable layer 108.

In a preffered embodiment, the release coating 104, coated on the inner surface of the release layer 102, renders the heat sealed area 118 peelable by weakening the thermal bond created therein. However, one alternative for achieving that result is to employ two different materials as the release alyer 102 and the heat sealable layer 108, such as polyethylene and polypropylene. In that case, no release coating 104 is required, and a weakened seal is created at 118 by the nature of the differences in physical properties as between these two layers. In any event, it is most important that this heat sealed area 1818 circumferentially separate the reservoir 114 from an extended peripheral area 120 of the release layer 102. The outer backing layer 110 and supported adhesive layer 112 have a sufficient surface area and are of a shape so that, when they are attached to the backing layer 106, they overlie at least a portion of the extended peripheral area 120. Thus, the adhesive layer 112 circumferentially surrounds the reservoir 114 and is isolated therefrom by the peelable heat sealed area 118. A medicament or active agent 122 is retained within the reservoir 114 by means of a sterile synthetic sponge 124 which facilitates the administration of the active agent to the skin or mucosa of a host. The sponge 124 is secured to the heat sealable layer 108 by means of, for example, one or more strips 126 of hot melt adhesive, or by other means of sealing, such as by ultrasonic welding, etc., or by applying strips of tape or the like, It can also be seen that the extended peripheral area 120 of release layer 102 extends outwardly beyond the outer backing layer 110 and its associated adhesive layer 112. This is done in this embodiment for the purpose of providing the equivalent of a tab for removal of the release layer 102 from the device.

During storage of the device 100, the active agent 122 within the reservoir 114 is isolated from contact with the adhesive layer 112 by means of heat sealed area 118. In this manner, as discussed above, contamination or deterioration of the adhesive layer 112 is prevented, as is contamination of the active agent by the adhesive layer. Furthermore, entrapment of the active agent within the adhesive layer during storage is also eliminated. However, the embodiment shown in FIG. 1 is particularly applied to use in connection with an active agent which will not migrate through or penetrate the heat sealed area 118. That, however, is not always the case, and where such migration or penetration is a potential problem for the particular active agent in question, the use of embodiment sof this invention as shown, for example, in FIGS. 2 and 3 hereof, is utilized in order to insure isolation of the active agent int he reservoir from the adhesive layer. These embodiments, and the use of an annular gap 140 for this purpose, are discussed more fully below. In adhering the device 100 to the skin or mucosa of a host, the release layer 102 is removed so as to expose the adhesive layer 112 as well as the sponge 124 containing the active agent 122. In this regard, the release coating 104 facilitates separation of the release layer 102 from the adhesive layer 112 and the heat sealed area 118. When the device 100 is adhered to the skin or mucosa by the surrounding adhesive layer 112, the active agent 122 within the sponge 124 is released to provide a direct continuous dose without having to permeate through the adhesive layer. Furthermore, by employing an active agent impermeable adhesive layer, there will continue to be no contamination or deterioration of the adhesive layer, or any contamination of the active agent after the device has been so applied.

Figure 2:
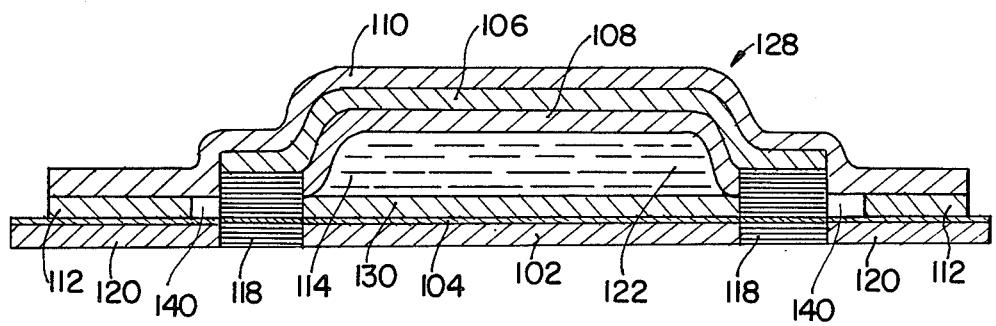
FIG. 2 is a side, elevational, cross-sectional view of another embodiment of a therapeutic device constructed in accordance with the present invention.

Turning now to FIG. 2, there is disclosed another embodiment of a therapeutic device constructed in accordance with the present invention, and in this case generally designated by reference numeral 128. The device 128 differs primarily from tht shown in FIG. 1 by the inclusion of a heat sealable permeable membrane 130, and by the inclusion of annular gap or space 140 between the heat sealed area 118 and the adhesive layer 112. The membrane 130 is provided between the release layer 102 and the reservoir 114, and is heat sealed about its perimeter within peelable heat sealed area 118 between the peripheral portion of release layer 120 and heat sealable layer 108. Thus, once again this portion of heat sealed area 118 between the release layer 102 and the membrane 130 is peelable by virtue of the presence of release coating 104 therebetween, sand its effect upon weakening of the thermal bond produced therebetween or by use of other methods for achieving this result, such as the use of differing thermoplastic layers as is discussed above, In any event, the thermal bond produced in heat sealed area 118 between the membrane 130 and the heat sealable layer 108 is not weakened in such manner, and is therefore a permanent bond or seal. The pressure sensitive adhesive layer 112 is interposed between the outer backing layer 110 and release layer 102 within the extended peripheral area 120 circumscribing the heat sealed area 118. In this case an annular gap 140 is also provided between the heat sealed area 118 and the ahdesive layer 112. Upon removal of the release layer 102 from the adhesive layer 112 and membrane 130, which is facilitated by the release coating 104, the active agent 122 can now be released through the membrane 130 to provide a continuous dose direction to the skin or mucosa of a host.

The membrane 130, in addition to being permeable, may be either microporous or macroporous, and the pores thereof therefore become filled with the active agent 122 from the reservoir 114. The membrane 130 may also function in any other way as long as the active agent 122 can permeate through the membrane, and this can occur at either a controlled (as with a microporous membrane) or a noncontrolled rate, as with a microporous membrane which merely permits the active agent to pass freely therethrough at a suitable rate. Materials suitable for use as the membrane 130 are conventional in the art and need not be discussed in detail here. Some preferred materials for the membrane 130 may be, for example, polypropylene, polycarbonates, polyvinyl chloride, cellulose acetate, cellulose nitrate, and polyacrylonitrile. It shall be noted that the use of such a membrane 130 itself necessitates the use of annular gap 140 to isolate the reservoirs in accordance with this invention, since but its very nature this membrane 130 must be permeable, and this will also be permeable to the active agent within the heat sealed area 118. Thus, without the presence of annular gap 140, the undesirable contact between the active agent and the adhesive layer 112 would take place.

Figure 3:
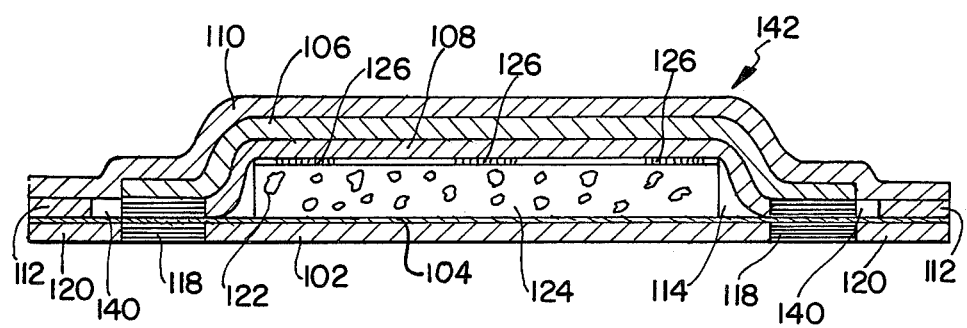
FIG. 3 is a side, elevational, cross-sectional view of another embodiment of a therapeutic device constructed in accordance with the present invention.

Turning to FIG. 3, this embodiment of a therapeutic device constructed in accordance with the present invention is generally designated by reference numeral 142. The device 142 differs primarily from that shown in FIG. 1 by elimination of the portion of the adhesive layer 112 covering the entire inner surface of outer backing layer 110. Thus, the adhesive layer 112 is limited in this case to the outer peripheral area thereof, i.e., outside of heat sealed area 118. Furthermore, annular ga 140 is again provided between the heat sealed area 118 and the adhesive layer 112 so as to further isolate the adhesive itself from the active agent.

In connection with these various embodiments, the backing layer 106 is preferably made of a material or combination of materials which are substantially impermeable to the layer or layers with which it can be in contact, i.e., to the active agent 122, the adhesive layer 112, etc. However, a primary prupose of the backing layer 106 is to prevent seepage of the active agent 122 from the reservoir 114. If the backing layer 106 is coated on its surface in contact with the active agent 122, such as by co-extrusion with the heat sealable layer 108, this co-extruded heat sealable layer will perform this purpose even if the backing layer per se is not totally impermeable to the active agent. Suitable materials for the heat sealable layer 108 include those polymers known as polyolefins, for example, polyethylene and polypropylene, and preferably an ethylene-vinyl acetate copolymer. Thus, it is not necessary in all instances that the backing layer 106 be impermeable to the active agent, although in most instances it normally is. This similarly applies to the outer backing layer 110 where that is utilized, which layer in FIG. 1 is rendered impermeable by its coating with the impermeable adhesive layer 112. By substantially impermeable, it is meant that the other components in contact with the layer or component under consideration will not appreciably permeate through such layer or component for the normal period of use and storage of the device.

The actual material used for the backing layer 106 and outer backing layer 108 will depend on the properites of the materials in contact therwith. Some suitable materials include, for example, cellophane, cellulose acetate, ethyl cellulose, plasticized vinyl acetate-vinyl chloride copolymers, ethylenevinyl acetate copolymer, polyethylene terephthalate, nylon, polyethylene, polypropylene, polyvinylidene chloride, and aluminum foil.

Preferably, the material which forms the backing layer 106 and heat sealable layer 108 are co-extruded to form an integral layer. The composite can be a metalized (e.g., aluminized) film or a laminate of two or more films or a combination thereof. For example, a laminate of polyethylene terephthalate and polyethylene or a polyethylene/metallized polyethylene terephthalate/-polyethylene laminate can be employed. The preferred polymers include polyethylene, polypropylene, polyvinyl chloride and polyethylene terephthalate.

A primary purpose of the adhesive layer 112 is to provide adhesion to the skin or mucosa, and the degree of impermeability of the adhesive layer 112 to the active agent 122 may vary, depending upon the active agent, carrier, transporting agent, etc. Preferably, the adhesive layer 112 is a pressure sensitive adhesive suitable for contact with the skin or mucosa, e.g., dermatologically acceptable. Examples of suitable pressure sensitive adhesives for use in the present invention as the active agent impermeable adhesive layer 112 include natural rubber adhesives such as R-1072 from B. F. Goodrich Co., No. 735 from C. L. Hawthaway, and No. 5702 from Evans-St. Clair; acrylic adhesives such as PS-41 from C. L. Hawthaway, VR-0833 from H. B. Fuller, Adcote 73A207A from Morton Chemical, Nos. 80-2404, 80-1054, 72-9056, and 72-9399 from National Starch, Nos. E-2015, E-2067 and E-1960 from Rohm & Haas, M-6112 from Uniroyal Inc. and Daratak 74 L from W. R. Grace; and synthetic rubber adhesives such as Jowatherm 270-00 and Jowatherm S-3202 from Jowat Corp. and 70-9416 from National Starch.

The active agents 122 suitable for use in the present invention may be, for example, systemic or topical drugs. Individual active agents 122 or mixtures thereof, if desired, can be employed. Any drug which passes through the skin or mucosa can be employed for internal administration in the devices 100, 128 and 142 of the present invention, so long as the drug will pass through the sponge 124, as shown in FIGS. 1 and 3 and/or the material forming the membrane 130, as shown in FIG. 2. Suitable systemic drugs for administration by the devices 100, 128 and 142 include those useful in treating emesis and nausea as is described in U.S. Pat. No. 4,031,894, e.g., preferably, scopolamine. Other suitable drugs include the coronary vasodilators described in U.S. Pat. No. 3,742,951, such as compounds having nitrate moiety. Still other suitable systemic drugs are disclosed in U.S. Pat. No. 3,996,934. Some examples of topical drugs suitable for use in the present invention include, for example, the folic acid antagonists, antineoplastic agents, and antimitotic agents described in U.S. Pat. No. 3,734,097.

The active agent 122 may be present in the reservoir 114 either alone or in combination with other active agents and/or a pharmaceutically acceptable carrier. Some suitable carriers are disclosed in U.S. Pat. No. 3,996,934. The active agent 122, whether in the presence or absence of a carrier, may also be combined in the reservoir 114 with a transporting agent which assists the drug delivery device to achieve the administration of a drug to a receptor such as by enhancing penetration through the skin. Some transporting agents suitable for use in the present invention include those described in U.S. Pat. No. 3,996,934.

The host to which an active agent 122 is administered by means of the therapeutic device 100, 128 may be any host on which a drug or other active agent has the desired effect. The host may be, for example, a mammal such as a human being, or, for that matter, any warm blooded or cold blooded animal. The advantage of administering the active agent 122 may be therapeutic or experimental. The devices 100, 128 and 142 of this invention may also be for any other advantageous purpose.

The degree of impermeability (for the impermeable adhesive layer 112 and for that matter the other elements of the devices 100, 128 and 142 which are desired to be impermeable to the active agent 122), is that degree which prevents the active agent from permeating or oozing away from the device during normal periods of use. The device preferably remains therapeutically effective for at least two years, more preferably at least five years, and most preferalby at least ten years.

It will be understood that the embodiments described herein are merely exemplary and that a person skilled in the art may make many variations and modifications without departing from the spirit and scope of the invention. All such modifications and variations are intended to be included within the scope of the invention as described in the appended claims.

What is claimed:

1. A device for the administration of an active agent to the skin or mucosa of a host comprising a reservoir containing said active agent, said reservoir including an inner surface and an outer surface, a release layer formed on said inner surface of said reservoir, and active agent impermeable backing layer formed on said outer surface of said reservoir, said backing layer overlying said release layer and sealed thereto about a circumferential sealed area so as to enclose said reservoir, said backing layer and said release layer extending peripherally beyond said sealed area about the entire periphery thereof so as to create an extended peripheral area, adhesive means disposed between said backing layer and said release layer in said extended peripheral area and thereby separated from said reservoir by said sealed area, said adhesive means addapted to adhere said device to the skin or mucosa of said host upon removal of said release layer, whereby said active agent is released from said reservoir to provide a dose of said active agent.

2. The device of claim 1 wherein said backing layer includes a heat sealable layer in contact with said release layer within said sealed area.

3. The device of claim 1 wherein said backing layer comprises a coextruded layer of a primary backing layer impermeable to said active agent and a heat sealable layer in contact with said release layer within said sealed area.

4. The device of claim 1 including a release coating provided on the inner surface of said release layer facing said reservoir and extending at least within said sealed area, whereby said release layer may be removed from said device for adhering said device to the skin or mucosa of said host by said adhesive means.

5. The device of claim 4 wherein said release coating further extends within said extended peripheral area to facilitate removal of said release layer from said adhesive means.

6. The device of claim 1 wherein said backing layer includes a primary backing layer impermeable to said active agent and extending at least to said sealed area and a secondary outer backing layer overlying said primary backing layer and said extended peripheral area.

7. The device of claim 6 wherein said secondary outer backing layer includes an inner surface and an outer surface, and said adhesive means comprising an adhesive layer extending over the entire inner surface of said secondary outer backing layer.

8. The device of claim 7 wherein said adhesive layer comprises an adhesive substantially impermeable to said active agent.

9. The device of claim 1 wherein said adhesive means comprises an adhesive layer comprising an adhesive substantially impermeable to said active agent.

10. The device of claim 1 further including an active agent permeable membrane disposed between said inner surface of said reservoir and said release layer, and extending at least to said sealed area so as to be sealed between said backing layer and said release layer.

11. The device of claim 1 or 10 including an annular gap in said extended peripheral area between said sealed area and said adhesive means so as to further separate said adhesive means from said reservoir.

12. The device of claim 1 wherein said reservoir contains a sponge for retaining said active agent therein.

13. The device of claim 1 wherein said sealed area comprises a peelable heat seal, whereby the removal of said release layer from said device can be facilitated.

14. The device of claim 1 wherein said release layer extends outwardly beyond said backing layer so as to act as a tab for removal of said release layer.

15. The device of claim 1 wherein said backing layer comprises a material selected from the group consisting of cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride and aluminum foil.

16. The device of claim 3 wherein said coextruded layer comprises a metalized film.

* * * * *

UNITED STATES PATENT AND TRADEMARK OFFICE
CERTIFICATE OF CORRECTION

PATENT NO. : 4,710,191

DATED : December 1, 1987

INVENTOR(S) : Kwiatek et al.

It is certified that error appears in the above-identified patent and that said Letters Patent is hereby corrected as shown below:

```
Column 1, line 19, "system" should read --systems--.
Column 1, lines 22-23, "scopolaimine" should read --scopolamine--.
Column 1, line 30, "containingg" should read --containing--.
Column 1, line 56, "effecitveness" should read --effectiveness--.
Column 2, line 26, "contaminationof" should read --contamination of--.
Column 2, line 27, "administratin" should read --administration--.
Column 4, line 57, "embodiment sof" should read --embodiments of--.
Column 4, line 59, "int he" should read --in the--.
Column 5, line 13, "tht" should read --that--.
Column 5, line 24, "sand" should read --and--.
Column 5, lines 41-42, "direction" should read --directly--.
Column 5, line 61, "but" should read --by--.
Column 6, line 7, "ga" should read --gap--.
Column 6, line 16, "prupose" should read --purpose--.
Column 6, line 40, "therwith" should read --therewith--.
Column 6, line 43, "ethylenevinyl" should read --ethylene-vinyl--.
Column 7, line 60, "preferalby" should read --preferably--.
Column 8, line 16, "addapted" should read --adapted--.
```

Signed and Sealed this

Twenty-fourth Day of May, 1988

Attest:

DONALD J. QUIGG

Attesting Officer

Commissioner of Patents and Trademarks